United States Patent [19]

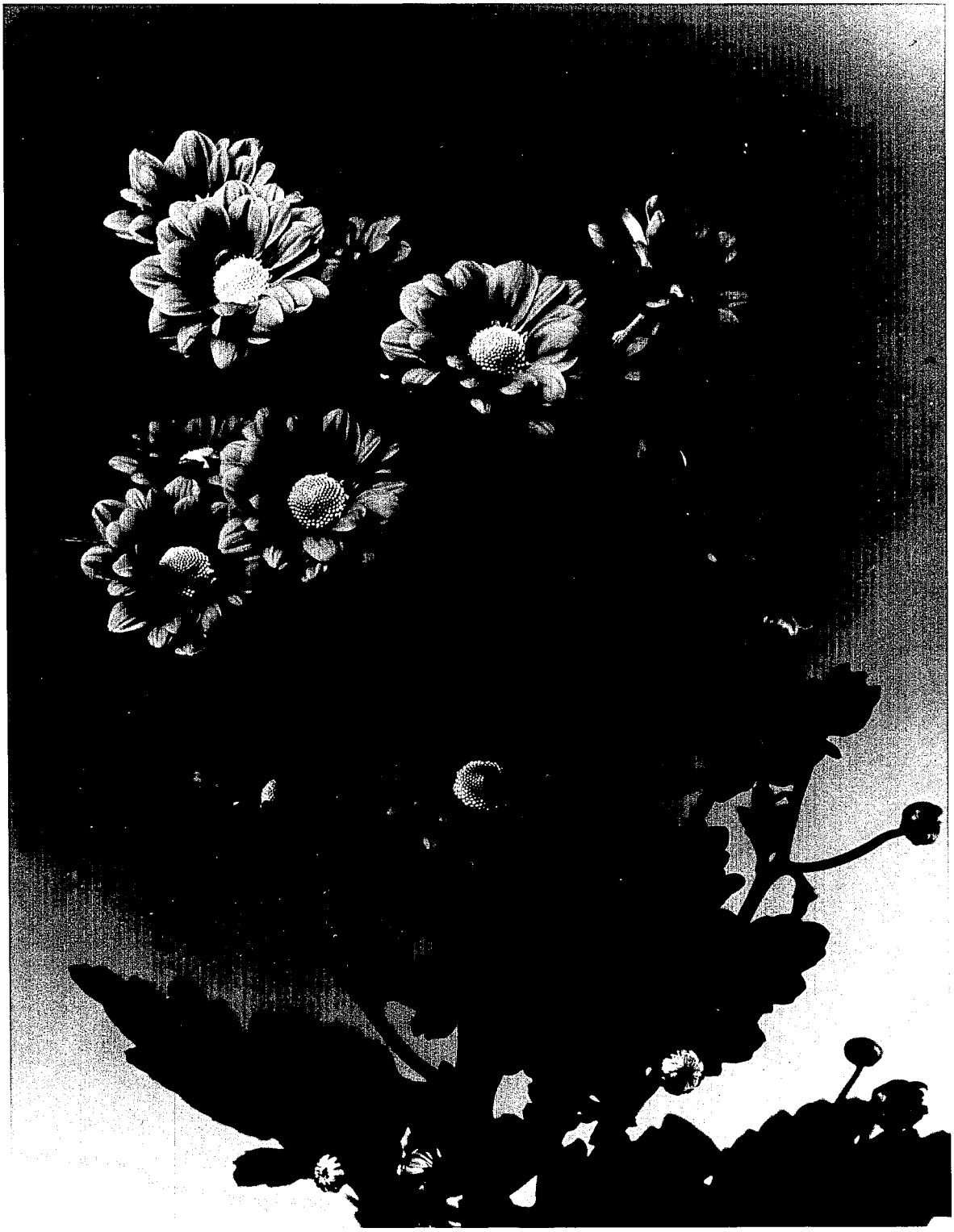

Van der Knaap

[11] Patent Number: Plant 6,736

[45] Date of Patent: Apr. 11, 1989

[54] CHRYSANTHEMUM PLANT NAMED KLONDIKE

[75] Inventor: Jacques C. M. Van der Knaap, De Lier, Netherlands

[73] Assignee: Fides Beheer B.V., De Lier, Netherlands

[21] Appl. No.: 123,903

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

The Chrysanthemum cultivar named Klondike is characterized by its flat capitulum form and single capitulum type, its red ray floret color which contrasts nicely with the yellow-green immature to yellow mature disc florets, and its 60–70 mm capitulum diameter.

1 Drawing Sheet

The present invention comprises a new and distinct cultivar of *Chrysanthemum morifolium,* hereinafter referred to by the cultivar name Klondike.

Klondike is a product of a planned breeding program which had the objective of creating new Chrysanthemum cultivars with single capitulum type, red ray floret color, eight (8) week response, low temperature tolerance, and the ability to produce commercially acceptable quality in year-round cut mum program. Such traits in combination were not present or needed improvement in previously available commercial cultivars.

Klondike was originated from a hybridization made by applicant in a controlled breeding program in De Lier, Holland in 1984. The female parent was Fame, U.S. Plant Pat. No. 4,785. The male parent of Klondike was Impala, disclosed in a pending application of applicant.

Klondike was discovered and selected as one flowering plant within the progeny of the stated parentage by Jacques C. M. Van der Knaap in July 1984 in a controlled environment in De Lier, Holland.

The first act of asexual reproduction of Klondike was accomplished when vegetative cuttings were taken from the initial selection in August 1984 in a controlled environment in De Lier, Holland by a technician working under formulations established and supervised by Jacques C. M. Van der Knaap. Horticultural examination of selected units initiated in April 1985 has demonstrated that the combination of characteristics as herein disclosed for Klondike are firmly fixed and are retained through successive generations of asexual reproduction.

Klondike has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Klondike, which in combination distinguish this Chrysanthemum as a new and distinct cultivar:

1. Flat capitulum form.
2. Single capitulum type.
3. Red ray florets.

4. Diameter across the face of the capitulum is 60–70 mm.
5. Yellow-green (immature) to yellow (mature) disc florets, which provide a pleasant contrast with the red ray floret color.
6. No abundant pollen production.

Of the many commercial cultivars known to the present inventor, the most similar in comparison to Klondike is Dark Lapana, an unpatented cultivar. In comparison to Dark Lapana, Klondike has smaller flowers, darker green foliage, and a much faster response (eight weeks instead of ten weeks). The disc floret color, capitulum form and capitulum type are similar to those same characteristics of Dark Lapana.

The accompanying photographic drawing is a side view showing typical inflorescence and foliage characteristics of Klondike, with colors being as nearly true as possible with illustrations of this type.

In the following description, color references are made to the Royal Horticultural Society Colour Chart. The color values were determined between 11:00 a.m. and 12:00 noon in June 1986 under natural daylight at De Lier, Holland.

Classification:

*Botanical.*—*Chrysanthemum morifolium,* Ramat., cv. Klondike.

*Commercial.*—Cut daisy spray.

INFLORESCENCE

A. Capitulum:

*Form.*—Flat.

*Type.*—Daisy.

*Diameter across face.*—60–70 mm.

B. Corolla of ray florets:

*Color (general tonality from a distance of three meters).*—Red.

*Color (upper surface).*—47A.

C. Corolla of disc florets:

*Color (mature).*—Yellow, approximately 7A.

*Color (immature).*—Yellow-green, approximately 145A.

D. Reproductive organs:

*Androecium.*—Present only in disc florets; numerous.

*Gynoecium.*—Present in both disc and ray florets; numerous.

PLANT

A. General appearance:
*Height.*—80 cm.
B. Foliage:
*Color* (*upper surface*).—147A.
*Color* (*under surface*).—147B.

*Shape.*—Pinnately lobed.

I claim:

1. A new and distinct cultivar of Chrysanthemum plant named Klondike, as illustrated and described, and parts thereof.

* * * * *